United States Patent [19]

Wallace et al.

[11] 4,424,208

[45] Jan. 3, 1984

[54] COLLAGEN IMPLANT MATERIAL AND METHOD FOR AUGMENTING SOFT TISSUE

[75] Inventors: Donald G. Wallace, Menlo Park; Susan B. Wade, Fremont, both of Calif.

[73] Assignee: Collagen Corporation, Palo Alto, Calif.

[21] Appl. No.: 338,661

[22] Filed: Jan. 11, 1982

[51] Int. Cl.³ .................... C07C 103/52; A61K 37/02
[52] U.S. Cl. ............................ 424/177; 260/112.5 R
[58] Field of Search .................. 424/177; 260/112.5 R

[56] References Cited

U.S. PATENT DOCUMENTS

| | | | |
|---|---|---|---|
| 3,548,056 | 12/1970 | Eigen et al. | 424/177 |
| 3,949,073 | 4/1976 | Daniels et al. | 424/177 |
| 4,060,081 | 11/1977 | Yannas et al. | 128/156 |
| 4,140,537 | 2/1979 | Luck et al. | 188/125 |
| 4,273,705 | 6/1981 | Kato | 424/177 |
| 4,279,812 | 7/1981 | Cioca | 424/177 |

OTHER PUBLICATIONS

Biomat., Med. Dev., Art. Org., 9 (1), 37-46, (1981).
J. Biomed Mater. Res., II, pp. 721, 724-741, (1977).
J.S.R., II, No. 1, 69-82, (1962).

Primary Examiner—Delbert R. Phillips
Assistant Examiner—F. T. Moezie
Attorney, Agent, or Firm—Ciotti & Murashige

[57] ABSTRACT

An injectable implant material for soft tissue augmentation comprising a dispersion of (a) particles of crosslinked atelopeptide collagen; and (b) reconstituted fibrous atelopeptide collagen in a (c) physiological aqueous carrier. Implants of this material have improved persistence relative to currently used collagen implant materials.

7 Claims, No Drawings

COLLAGEN IMPLANT MATERIAL AND METHOD FOR AUGMENTING SOFT TISSUE

DESCRIPTION

1. Technical Field

The invention is in the field of body treating compositions and methods. More particularly it concerns a collagen implant material of improved volume stability for augmenting soft tissue in mammals.

2. Background Art

Collagen has been used as a pharmaceutical carrier, as a surgical prosthesis (sutures and wound dressings), and as an implant material. In many instances the collagen is cross-linked with chemical agents, radiation, or other means to improve its mechanical properties, decrease its immunogenicity, and/or increase its resistance to resorption.

U.S. Pat. No. 3,949,073 describes the use of atelopeptide solutions of collagen as an injectable implant material for augmenting soft tissue. According to the patent, the collagen is reconstituted before implantation and forms a fibrous mass of tissue when implanted. The patent suggests adding particles of insoluble collagen microfibrils to control the shrinkage of the fibrous mass formed at the augmentation site. ZYDERM collagen implant is a commercial embodiment of the material described in the patent and is composed of reconstituted atelopeptide collagen in saline that contains a small amount of a local anesthetic. While this commercial material is remarkably effective, it may shrink in volume after implantation due primarily to absorption of its fluid component by the body. Thus, if volume constancy, sometimes called "persistency", is essential, an additional injection or injections of supplemental implant material is required. The present invention provides a collagenous implant material having improved volume stability or "persistence".

DISCLOSURE OF THE INVENTION

The implant material of this invention is an injectable dispersion of:
(a) particulate cross-linked atelopeptide collagen; and
(b) reconstituted atelopeptide collagen fibers; dispersed in
(c) an aqueous carrier.

This material is used to augment soft tissue by injecting it at the augmentation site. It provides an implant having substantially improved persistence relative to the currently used collagen implant material.

MODES FOR CARRYING OUT THE INVENTION

The noncross-linked and cross-linked forms of collagen used in the invention may be derived from collagen collected from any number of mammalian sources. The donor need not be genetically similar to the host into which the material is ultimately implanted. Because of their availability, bovine or porcine corium will usually be employed. The first step in making either form is to prepare atelopeptide collagen in solution from the corium. The animal skin is softened by soaking it in a mild acid and then scraping it to remove hair, epidermis, and fat. The depilated skin is then soaked again in mild acid and then comminuted by grinding, mincing, milling or like physical treatment. The comminution prepares the skin for solubilization.

The divided tissue may be solubilized under nondenaturing conditions by dispersing it in an aqueous acid medium and digesting it with a proteolytic enzyme other than a collagenase. Dilute acid solution at low temperatures will normally be used to avoid denaturation. Mineral acids such as HCl or carboxylic acids such as acetic, malonic or lactic acids may be used at pHs in the range of about 1.5 to 5 and temperatures of about 5° C. to 25° C. A preferred procedure is to disperse the comminuted tissue in HCl to a concentration of 1 to 5 g/l at a pH of about 2 at 20° C. After the tissue is dispersed the enzyme is added and the mixture is incubated to permit the enzyme to digest the telopeptide and other solubilizable components of the tissue. Enzymes that attack the telopeptide portion of the collagen while not denaturing the helical portion are used. Examples of such enzymes are trypsin, pepsin, chymotrypsin, and papain. Pepsin is preferred because it is relatively easily deactivated and removed from the solubilized collagen. The enzyme concentration will usually be in the range of about 0.1% to 10% by weight based on the collagen. The incubation period will typically vary from about two days to two weeks. The progress of the solubilization may be monitored by determining the viscosity of the solution. Once the viscosity reaches a substantially constant level, the solubilization is complete. At this point, the enzyme is deactivated (denatured) and removed.

The enzyme may be deactivated by raising the pH of the solution to at least about 7 by adding an alkaline material such as sodium hydroxide. After the enzyme has been denatured the solution is treated to remove denatured enzyme and the portions of the tissue that were digested during the solubilization. Various dialysis, sedimentation, and filtration techniques may be used to effect such removal. See U.S. Pat. No. 949,073 col 3, lines 10-22 and U.S. Pat. No. 4,140,537 col 5, line 48 to col 6, line 34, which disclosures are incorporated herein by reference. A preferred procedure is to first lower the pH by adding acid and then clarify the solution by diatomaceous earth sedimentation. The sediment is filtered and the filtrate is concentrated. The concentrate is then fractionated by ion exchange chromatography and further concentrated to produce a substantially pure atelopeptide collagen solution that may be used to make the cross-linked collagen and the noncross-linked collagen fibers used in the invention.

The fibrous collagen is preferably made by neutralizing the solution with buffer at reduced temperatures. The ionic strength of the neutralized solution is about 0.03 to 0.3 and the pH is about 7.2 to 7.4. $Na_2HPO_4$ is a preferred buffer. This increase in pH causes the collagen to reaggregate into atelopeptide fibrils. These fibrils are separated from the supernatant for combination with the cross-linked gel particles.

The cross-linked particles are made from the solution by first reconstituting the collagen and then cross-linking the reconstituted material. The reconstitution is preferably carried out by increasing the pH of the solution to about 7.4 to 7.6 by adding buffers and base at a reduced temperature and then raising the temperature to a suitable temperature ie 26° C. to 38° C. The collagen reaggregates spontaneously under such conditions. After the reconstituted collagen is formed it is cross-linked by exposing it to a cross-linking agent that forms covalent bonds between collagen chains. Radiation-induced cross-linking or chemical induced cross-linking may be used. Either nonparticulate radiation (ultraviolet, gamma, X-ray) or particulate radiation (α-particles, protons, β-particles, electrons) may be used. Chemical cross-linking agents that may be used include those that are commonly used to cross-link proteins for medical use such as formaldehyde, glutaraldehyde, acetaldehyde, glyoxal pyruvic aldehyde, dialdehyde starch, quinones, hydroquinones, dimethylol acetone, and divinyl sulfone. Glutaraldehyde is a preferred cross-linking agent.

The conditions of cross-linking, particularly the concentration of cross-linking agent the temperature, and the duration of the reaction, will affect the degree to which the collagen is cross-linked. The degree of cross-linking is commonly expressed indirectly in terms of physical measurements such as molecular weight changes, gelation characteristics, swelling properties or tensile properties such as Young's modulus. The conditions and agent are preferably such as to give a cross-linked material having a Young's modulus in the range of about 1,000 to 10,000 dynes/$cm^2$ before it is concentrated by centrifuging and about 5,000 to 50,000 dynes/$cm^2$ after centrifuging as described below. When glutaraldehyde is employed, reaction with about 0.004 to 4 mg of glutaraldehyde per g of collagen gel at 15° C. to 30° C. for about ½ to 20 hr will provide suitable cross-linking. The glutaraldehyde will normally be added to the gel as a dilute aqueous solution. After the desired reaction period the cross-linked gel is washed to remove any cross-linking agent and is then concentrated by filtration or centrifugation to about 10 to 100 mg protein/ml. The concentrated gel is then subjected to mild shear stress to comminute it into uniform particles about 50 to about 200 microns in equivalent spherical diameter. A high speed grater or knife mill may be used to comminute the gel.

The fibrous collagen and cross-linked collagen particles are dispersed in an appropriate aqueous parenteral carrier. The dispersion is placed in a syringe or other injection apparatus. The fibrous collagen will usually constitute about 5% to 30% by weight of the total collagen in the dispersion, preferably 15% to 25% by weight and the cross-linked gel will usually constitute about 70% to 98% by weight of the total collagen in the dispersion, preferably 75% to 85% by weight. A particularly preferred dispersion contains the fibrous collagen and cross-linked collagen in a 20:80 weight ratio. Minor amounts of additives such as local anesthetics may be included in the implant composition. The aqueous carrier should be a medium that is physiologically acceptable to the host. Thus, its ionic strength and pH should be physiological (ie pH 6.8 to 7.5, ionic strength 0.1 to 0.2). Saline is a preferred carrier. The total collagen concentration in the dispersion will usually be in the range of about 15 to about 80 mg/ml, preferably 40 to 60 mg/ml.

The above described collagen implant material may be injected intradermally to augment soft tissue, to repair or correct congenital anomalies, acquired defects or cosmetic defects. Examples of such conditions are congenital anomalies such as hemifacial microsomia, malar and zygomatic hypoplasia, unilateral mammary hypoplasia, pectus excavatum, pectoralis agenesis (Poland's anomaly). and velopharyngeal incompetence secondary to cleft palate repair or submucous cleft palate (as a retropharyngeal implant); acquired defects (post traumatic, post surgical, post infectious) such as depressed scars, subcutaneous atrophy (eg, secondary to discoid lupis erythematosis), enophthalmos in the enucleated eye (also superior sulcus syndrome), acne pitting of the face, linear scleroderma with subcutaneous atrophy, saddlenose deformity, Romberg's disease and unilateral vocal cord paralysis; and cosmetic defects such as glabellar frown lines, deep nasolabial creases, circum-oral geographical wrinkles, sunken cheeks and mammary hypoplasia.

The following examples illustrate the implant materials, the method by which they are used, and the merits of implants made of these materials. These examples are not intended to limit the invention in any manner.

MATERIALS AND METHODS

Preparation of Atelopeptide Bovine Collagen Solution

Bovine hide was softened and depilated by treatment with acetic acid. The hide was then comminuted and dispersed in HCl, pH 2, at 8–11 g/l. Pepsin was added to the dispersion at 0.1% by weight based on total protein and the mixture was allowed to incubate for about 100–300 hr at 15° C. to 20° C. NaOH was then added to raise the pH of the incubation medium to about 7 and thereby terminate the digestion. The denatured enzyme was removed from the reaction mixture by sedimentation at reduced pH. The solution was then purified and concentrated by filtration and chromatography to form a 3 mg/ml solution of atelopeptide bovine collagen in dilute aqueous HCl, pH 2. This solution is hereinafter referred to as CIS.

Preparation of Fibrous Collagen

Fibrous collagen was reconstituted from CIS by adding 0.02 M $Na_2HPO_4$, to the CIS at 18° C. to increase its pH to 7.4. The precipitated fibrous collagen was separated from the supernatant, concentrated, and homogenized with NaCl and $Na_2HPO_4$ to a physiological pH and ionic strength. The concentration of collagen in the resulting dispersion was 35 mg/ml.

Preparation of Cross-linked Gel Particles

CIS was mixed at 0° C. with a buffer composed of 1.3 M NaCl and 0.2 M $Na_2HPO_4$ and the pH of the mixture was rasied to 7.4–7.6 with 0.1 N NaOH. The temperature of the mixture was then raised to 34° C. and held there for two hours during which time the solution gelled.

The gel was added to a 0.4% by weight solution of glutaraldehyde in physiological phosphate buffer, pH 7.4 (280 mg glutaraldehyde per g of collagen in the gel) and allowed to react for one hour. The resulting cross-linked gel was washed repeatedly with the phosphate buffer to remove the aldehyde. The gel was then centrifuged until a protein concentration of approximately 30 mg/ml (determined by quantitative ninhydrin assay) was reached. A sample of the gel was removed and its Young's modulus was determined by the methods described in Mechanical Properties of Polymers and Composites, Vol. 1, Dekker, New York 1974, pp 1–50 and Gordon, et al, Nature 217: 735 (1968).

Comminution of the centrifuged collagen was carried out by one of several methods depending upon the toughness of the gel. Low strength materials could be fragmented or shredded by extruding back and forth between two syringes joined by a #12 gauge bore tube. Stronger gels required mincing into strips before applying the double syringe method. Once the cross-linked preparations were homogenized, fibrous collagen could be mixed with them and further homogenized by passage between syringes.

Preparation of Implant Materials

The fibrous collagen dispersion was mixed with the cross-linked collagen gel particles in various proportions and the mixtures were placed in sterile syringes. Control materials of only the dispersion and only the gel were also placed in sterile syringes.

Implantation

Sprague Dawley female rats weighing 125±20 g were used as hosts.

Each rat was implanted in two sites, fibrous collagen alone as control in the left dorsal cranial region, and glutaraldehyde cross-linked collagen with or without admixed fibrous collagen in the right dorsal cranial regions. Injections were through #18 gauge needles into the subcutaneum. Injection of the cross-linked collagen alone was difficult. Weighed quantities (usually about 0.5 g) were delivered.

Explanation of paired experimental and control samples was carried out at intervals ranging from 5 to 50 days. Host tissue was carefully dissected from collagen implants, and the wet weights were recorded. The percent weight recovery (persistence) was then calculated from the weight implanted. Weighed specimens were then embedded, sectioned, and stained for histological examination. Stains used included hematoxylin and eosin, trichrome, and von Kossa.

Results

The table below presents the results of the implantation of the implant materials of the invention and the control implant materials.

| | Material | Biocompatibility | Persistance (%) |
|---|---|---|---|
| 1. | Fibrous Collagen Alone (35 mg/protein/ml) | Modest cell invasion, vascularization, generally acceptable | 36 ± 6 |
| 2. | Cross-linked Collagen (57 mg protein/ml). | More extensive cell invasion and vascularization, acceptable | 108 ± 19 |
| 3. | Cross-linked Collagen plus Fibrous Collagen (80:20; w/w; total mg protein/ml:53) | Similar to 2, but fewer cells, acceptable | 89 ± 2 |

As indicated by the above results, the implant material made from the combination of noncross-linked fibrous collagen and cross-linked collagen has substantially better persistence than the implant containing only noncross-linked fibrous collagen. While the persistence of the cross-linked collagen implant was even better, the injectability of this material is poor. The injectability of the implant made from the combination noncross-linked and cross-linked collagen was acceptable.

Histologically all three materials were biocompatable. The implant containing cross-linked collagen were invaded by more cells and vascularized more rapidly than fibrous collagen alone. New collagen synthesis appeared to be occurring in the cross-linked collagen; presumably this explains the increase in weight of such explants. At early time points some cell types associated with an inflammatory response appeared in cross-linked samples. At later times the cells were primarily fibroblasts, which are indicative of a beneficent colonization.

Modifications of the above described embodiments of the invention that are obvious to those of skill in the biochemical, medical, and/or surgical arts are intended to be within the scope of the following claims.

We claim:

1. An injectable implant material for soft tissue augmentation comprising a dispersion of:
   (a) particulate cross-linked atelopeptide collagen; and
   (b) reconstituted fibrous atelopeptide collagen; dispersed in
   (c) an aqueous carrier wherein the total collagen in the dispersion is in the range of about 15 to about 80 mg/ml, the cross-linked collagen constitutes about 70% to 95% by weight of the total collagen in the dispersion and the fibrous collagen constitutes about 5% to about 30% by weight of the total collagen in the dispersion.

2. The implant material of claim 1 wherein said carrier has a substantially physiological pH and ionic strength.

3. The implant material of claim 1 wherein the particle size of the cross-linked collagen is in the range of about 50 to about 200 microns and the cross-linked collagen has a Young's modulus of about 5,000 to about 50,000 dynes/cm$^2$.

4. The implant material of claim 3 wherein the cross-linked collagen is cross-linked with glutaraldehyde.

5. The implant material of claim 1 wherein the carrier has a substantially physiological pH and ionic strength; the total collagen in the dispersion is in the range of 40 to 60 mg/ml; the cross-linked collagen constitutes 75% to 85% by weight of the total collagen in the dispersion and the fibrous collagen constitutes 15% to 25% by weight of the total collagen in the dispersion; and the cross-linked collagen has a particle size in the range of about 50 to about 200 microns and a Young's modulus of about 5,000 to 50,000 dynes/cm$^2$.

6. The implant material of claim 1 or 5 wherein the dispersion includes
   (d) a local anesthetic.

7. A method for augmenting soft tissue in a living mammal comprising injecting the material of claim 1 or 7 into the mammal at the augmentation site.

* * * * *